(12) United States Patent
Aurrecoechea et al.

(10) Patent No.: US 7,129,215 B2
(45) Date of Patent: Oct. 31, 2006

(54) TRIPEPTIDE AND TETRAPEPTIDE THIOETHERS

(75) Inventors: Natalia Aurrecoechea, Oakland, CA (US); Andrew B. Kelson, San Carlos, CA (US); Robert W. Macsata, Pleasanton, CA (US); Louise Robinson, San Carlos, CA (US); Anthony J. Sanchez, Oakland, CA (US); Nicholas M. Santiago, San Francisco, CA (US); Steven R. Schow, Redwood City, CA (US); Reyna J. Simon, Los Gatos, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 11/325,846

(22) Filed: Jan. 4, 2006

(65) Prior Publication Data

US 2006/0160749 A1    Jul. 20, 2006

Related U.S. Application Data

(60) Provisional application No. 60/641,932, filed on Jan. 6, 2005.

(51) Int. Cl.
*A61K 38/05*    (2006.01)
*A61K 38/06*    (2006.01)
*C07K 5/02*    (2006.01)

(52) U.S. Cl. .................. 514/18; 530/330; 530/331

(58) Field of Classification Search .................. None
See application file for complete search history.

(56) References Cited

U.S. PATENT DOCUMENTS

| | | |
|---|---|---|
| 5,556,942 A | 9/1996 | Kauvar et al. |
| 5,599,903 A | 2/1997 | Kauvar et al. |
| 5,763,570 A | 6/1998 | Kauvar et al. |
| 5,767,086 A | 6/1998 | Kauvar et al. |
| 5,786,336 A * | 7/1998 | Kauvar et al. ............. 514/18 |
| 5,955,432 A | 9/1999 | Kauvar et al. |
| 6,627,732 B1 | 9/2003 | Sakon et al. |
| 7,029,695 B1 * | 4/2006 | Redelmeier et al. ......... 424/450 |

| | | |
|---|---|---|
| 2003/0100511 A1 | 5/2003 | Kauvar et al. |

FOREIGN PATENT DOCUMENTS

| | | |
|---|---|---|
| EP | 0645397 B1 | 9/1998 |
| WO | WO95/08563 | 3/1995 |
| WO | WO 95/09865 | 4/1995 |
| WO | WO 95/09866 | 4/1995 |
| WO | WO96/40205 | 12/1996 |
| WO | WO 98/09986 | 3/1998 |
| WO | WO99/54346 | 10/1999 |
| WO | WO00/44366 | 8/2000 |

OTHER PUBLICATIONS

Hamilton & Batist "TLK-199" IDrugs, 2005, 8(8), 662-669.*
U.S. Appl. No. 11/326,975, filed Jan. 5, 1996, Steven R. Schow.
Ciaccio et al., "Modulation of detoxification gene expression in human colon HT29 cells by glutathione S-transferase inhibitors", Mol. Pharmacol., 48(4), 639-647 (1995).
Johansson et al., "The human glutathione transferase P1-1 specific inhibitor TER117 designed for overcoming cytostatic-drug resistance is also a strong inhibitor of glyoxalase I", Mol. Pharmacol., 57, 69-624 (2000).
Lyttle et al., "Isozyme-specific glutathione S-transferase inhibitors: design and synthesis", J. Med. Chem., 37(1), 189-194 (1994).
Lyttle et al., "Glutathione S-transferase activates novel alkylating agents", J. Med. Chem., 37(10), 1501-1507 (1994).
Shiotsuki et al., "Inhibition of glutathione transferase by S-benzyl glutathione analogous to the conjugate of saligenin cyclic phosphate", Pestic. Biochem. Physiol., 37(2), 121-129 (1990).
Townsend et al., Efficacy of a Glutathione S-Transferase π-activated Prodrug in Platinum-resistant Ovarian Cancer Cells: *Molecular Cancer Therapeutics*. (Oct. 2002) 1:1089-1095.
Vince et al., "Studies on the inhibition of glyoxalase I by S-substituted glutathiones", J. Med. Chem., 14(5), 402-404 (1971).

* cited by examiner

*Primary Examiner*—Cecilia J. Tsang
(74) *Attorney, Agent, or Firm*—Foley & Lardner LLP

(57) ABSTRACT

Tripeptide and tetrapeptide thioethers, pharmaceutical compositions containing them, their pharmaceutical use, and their preparation. The compounds are useful in potentiating the cytotoxic effects of chemotherapeutic agents in tumor cells, selectively exerting toxicity in tumor cells, elevating the production of GM progenitors in bone marrow, stimulating the differentiation of bone marrow, mitigating the myelosuppressive effects of chemotherapeutic agents, and modulating hematopoiesis in bone marrow.

24 Claims, No Drawings

TRIPEPTIDE AND TETRAPEPTIDE THIOETHERS

CROSS-REFERENCE TO RELATED APPLICATION

This application claims the priority under 35 USC 119(e) of U.S. Provisional Application No. 60/641,932, filed 6 Jan. 2005, which is incorporated into this application by reference.

BACKGROUND OF THE INVENTION

1. Field of the Invention

This invention relates to tripeptide and tetrapeptide thioethers, pharmaceutical compositions containing them, their pharmaceutical use, and their preparation.

2. Description of the Related Art

U.S. Pat. Nos. 5,599,903; 5,763,570; 5767086; 5786336; and 5955432; European Patent Publication No. 0 645 397; and PCT International Publications Nos. WO 95/08563 and WO 96/40205 disclose various tripeptide and tetrapeptide compounds that are analogs of reduced glutathione (L-γ-glutamyl-L-cysteinylglycine), including compounds of the formula [WO 95/08563]:

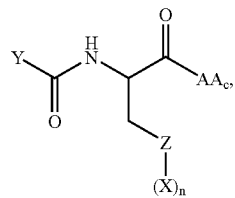

and their $C_{1-10}$ alkyl or alkenyl or $C_{7-12}$ aralkyl esters, amides, and mixed ester/amides, where:

Z is S, O, or C;

n is 1 to 3;

when Z is S or O and n is 1, X is a $C_{1-20}$ hydrocarbyl optionally containing 1 or 2 non-adjacent O, S, or N heteroatoms, unsubstituted or mono- or disubstituted with halo, —NO, —NO$_2$, —NR$_2$, —OR, or —SR, where R is H or $C_{1-4}$ alkyl;

when Z is S and n is 2, one X is as above defined and the other X is $C_{1-4}$ alkyl; and when Z is C and n is 3, one X is as above defined and the other two X are independently H or $C_{1-4}$ alkyl;

YCO is γ-glu, β-asp, glu, asp, γ-glu-gly, β-asp-gly, glu-gly, asp-gly; and $AA_c$ is an amino acid coupled through a peptide bond to the remainder of the compound.

The compounds are described as having various uses, including as reagents useful in characterizing glutathione S-transferase (GST) isoenzymes, in determining the GST complements of cells and tissues, as chromatographic affinity ligands, binding agents, and enzyme inhibitors; and therapeutically to: potentiate the cytotoxic effects of chemotherapeutic agents in tumor cells, selectively exert cytotoxicity in tumor cells, elevate the production of granulocyte-mactophage (GM) progenitors in bone marrow, stimulate the differentiation of bone marrow cells, mitigate the bone marrow-destructive effects of chemotherapeutic agents, and modulate hematopoiesis in bone marrow.

TLK117, identified in those patents and publications as TER 117 and named variously as γ-Glu-Cys(Bz)-phenylGly, γE-C(Bz)-φG, γE-C(Bz)-PG, γE-C(benzyl)-φG, and benzyl PG, is one of these compounds. TLK117 is the compound of the formula

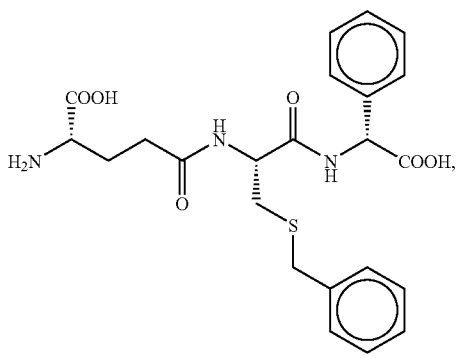

and may be named L-γ-glutamyl-S-(phenylmethyl)-L-cysteinyl-D-phenylglycine. TLK117 inhibits GST P1-1 with an $IC_{50}$ of approximately 400 nM. TLK199, identified in those patents and publications as TER 199, is the diethyl ester of TLK117.

U.S. Pat. No. 6,627,732 and PCT International Publication No. WO 99/54346 disclose glutathione derivatives of the formula

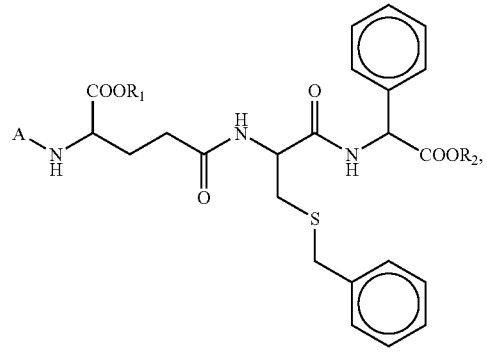

where

A is H or $C_{1-20}$ acyl;

$R_1$ is $C_{1-26}$ alkyl or $C_{3-26}$ alkenyl; and $R_2$ is H, $C_{1-26}$ alkyl, or $C_{3-26}$ alkenyl;

excluding the case where $R_1$ is $C_{1-10}$ alkyl or $C_{3-10}$ alkenyl and $R_2$ is H, $C_{1-10}$ alkyl or $C_{3-10}$ alkenyl.

US Published Application No. 2003/0100511 and PCT International Publication No. WO 00/44366 disclose lipid formulations, including liposomal formulations, of diesters of compounds of the formula:

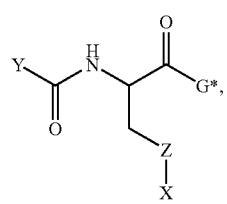

where:

each ester is 1–25C;

YCO is γ-glu or β-asp;

G* is phenylglycine;

Z is $CH_2$, O, or S; and

X is 6–8C alkyl, benzyl, or naphthyl, or a pharmaceutically acceptable salt thereof; or a compound of the formula:

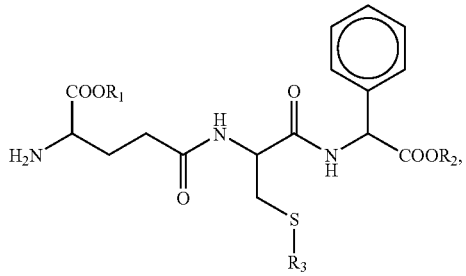

where:

$R_1$ and $R_2$ are independently chosen from linear or branched alkyl groups (1–25C), cycloalkyl groups (6–25C), substituted alkyl groups (2–25C), heterocycles (6–20C), ethers or polyethers (3–25C), or where $R_1$–$R_2$ (2–20C) together form a macrocycle with the formula; and $R_3$ is 6–8C alkyl, benzyl, or naphthyl, or a pharmaceutically acceptable salt thereof.

Many conditions are characterized by depleted bone marrow, including myelodysplastic syndrome (MDS), a form of pre-leukemia in which the bone marrow produces insufficient levels of one or more of the three major blood elements (white blood cells, red blood cells and platelets). A reduction in blood cell levels and the generation of new blood cells in the bone marrow, myelosuppression, is also a common, toxic effect of many standard chemotherapeutic drugs.

TLK199 has been shown to induce the differentiation of HL-60 promyelocytic leukemia cells in vitro, to potentiate the activity of cytotoxic agents both in vitro and in vivo, and to stimulate colony formation of all three lineages of hematopoietic progenitor cells in normal human peripheral blood. In preclinical testing, TLK199 has been shown to increase white blood cell production in normal animals as well as in animals in which white blood cells were depleted by treatment with cisplatin or fluorouracil. Similar effects may provide a new approach to treating MDS. TLK199 is currently being evaluated in a Phase II clinical trial for the treatment of MDS. Interim results from this trial, reported at the 2004 and 2005 American Society of Hematology meetings, demonstrated that TLK199 was well tolerated and resulted in multilineage hematologic improvement. These results also suggest a potential role for TLK199 in treating chemotherapy-induced cytopenias.

It would be desirable to develop potent inhibitors of GST P1-1 for use in humans to: potentiate the cytotoxic effects of chemotherapeutic agents in tumor cells, selectively exert cytotoxicity in tumor cells, elevate the production of GM progenitors in bone marrow, stimulate the differentiation of bone marrow, mitigate the myelosuppressive effects of chemotherapeutic agents, and modulate hematopoiesis in bone marrow.

SUMMARY OF THE INVENTION

In a first aspect, this invention is compounds of the formula

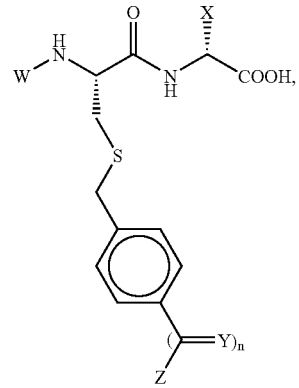

where:

n is 0 or 1;

W is L-γ-glutamyl or L-γ-glutamylglycyl;

X is optionally substituted $C_{5-6}$ cycloalkyl, optionally substituted $C_{5-6}$ heterocycloalkyl, optionally substituted phenyl, or optionally substituted $C_{5-6}$ heteroaryl;

Y is =O, =N—OH, or =N—O(optionally substituted $C_{1-3}$ alkyl); and

Z is optionally substituted phenyl or optionally substituted $C_{5-6}$ heteroaryl;

and their $C_{1-10}$ alkyl, (phenyl)-$C_{1-3}$ alkyl, or ($C_{5-6}$ heteroaryl)-$C_{1-3}$ alkyl mono- and di-esters;

and salts of the compounds and their mono- and di-esters.

The compounds (especially in the acid form) are very potent inhibitors, typically selective inhibitors, of GST P1-1 in vitro. In the diester form, they have also been shown to be effective in the immunoprecipitation of GSTπ from HL-60 cells in vitro, and to be cytotoxic to HL-60 cells in vitro. From this and from the structural similarity to TLK117, TLK199, and related compounds, the compounds are therefore expected to act therapeutically to: potentiate the cytotoxic effects of chemotherapeutic agents in tumor cells, selectively exert cytotoxicity in tumor cells, elevate the production of GM progenitors in bone marrow, stimulate the differentiation of bone marrow, mitigate the myelosuppressive effects of chemotherapeutic agents, and modulate hematopoiesis in bone marrow.

In a second aspect, this invention is pharmaceutical compositions comprising compounds of the first aspect of this invention, and optionally one or more excipients.

In a third aspect, this invention is therapeutic methods, particularly in a human, of one or more of: potentiating the cytotoxic effects of chemotherapeutic agents in tumor cells, selectively exerting toxicity in tumor cells, elevating the production of GM progenitors in bone marrow, stimulating the differentiation of bone marrow, mitigating the myelosuppressive effects of chemotherapeutic agents, and modulating hematopoiesis in bone marrow, by the administration of compounds of the first aspect of this invention or a pharmaceutical composition of the second aspect of this invention, and the use of the compounds of the first aspects of this invention in the manufacture of a medicament for one or more of the therapeutic methods mentioned above.

In a fourth aspect, this invention is compounds of the formula

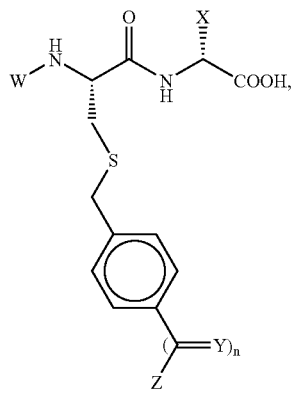

where:

W is N-α-R$^1$-L-γ-glutamyl or N-α-R$^1$-L-γ-glutamylglycyl, where R$^1$ is an amine-protecting group; and n, X, Y, and Z are as defined in claim 1;

and their $C_{1-10}$ alkyl, phenyl-$C_{1-3}$ alkyl, or ($C_{5-6}$ heteroaryl)-$C_{1-3}$ alkyl mono- and di-esters;

and salts of the compounds and their mono- and di-esters.

These compounds are useful as intermediates in the preparation of the compounds of the first aspect of this invention.

In a fifth aspect, this invention is methods of synthesis of the compounds of the first aspect of this invention.

Preferred embodiments of this invention are characterized by the specification and by the features of claims 2–21 of this application as filed, and of pharmaceutical compositions and methods of using these compounds.

DETAILED DESCRIPTION OF THE INVENTION

Definitions

"Alkyl" means a monovalent group derived from a saturated or unsaturated (but not aromatically unsaturated), hydrocarbon that may be linear, branched, or cyclic by removal of one hydrogen atom from a carbon atom, such as methyl, ethyl, propyl, 1-propenyl, isopropyl, butyl, isobutyl, sec-butyl, tert-butyl, pentyl, hexyl, cyclopentyl, cyclopenten-1-yl, cyclopropylmethyl, cyclohexyl, and cyclohexylmethyl. Saturated alkyls and $C_{1-6}$ alkyls are exemplary. Note that the definition of "alkyl" in this application is broader than the conventional definition and includes groups more commonly referred to as "cycloalkyl", "cycloalkylalkyl", "alkenyl", and "alkynyl".

"Substituted $C_{1-3}$ alkyl" (in the definition of Y) means $C_{1-3}$ alkyl substituted with 1 or 2, especially 1, groups selected from halo, hydroxy, methyl, trifluoromethyl, methoxy, and amino.

"Substituted $C_{5-6}$ cycloalkyl" means cyclopentyl or cyclohexyl, substituted with 1 or 2, especially 1, groups selected from halo, hydroxy, methyl, trifluoromethyl, and methoxy, especially F, Cl, or methyl.

"$C_{5-6}$ Heterocycloalkyl" means cyclopentyl or cyclohexyl in which 1 of the ring methylene groups is replaced by O, S, $SO_2$, NH, or N-methyl; and includes 2- and 3-tetrahydrofuryl, 3- and 4-tetrahydropyranyl, 4-tetrahydrothiopyranyl and its S,S-dioxide, and 2-, 3-, and 4-piperidinyl. "Substituted $C_{5-6}$ heterocycloalkyl" means $C_{5-6}$ heterocycloalkyl substituted in the same manner described above for substituted $C_{5-6}$ cycloalkyl.

"Substituted phenyl" means phenyl substituted with up to 3 substituents selected from halo, —CN, —$NO_2$, —OH, optionally halo-substituted $C_{1-3}$ alkyl (e.g. ethyl, trifluoromethyl), optionally halo-substituted $C_{1-3}$ alkyloxy, formyl, carboxy, and $C_{1-3}$ alkoxycarbonyl.

"Halogen" or "halo" means F, Cl, or Br.

"$C_{5-6}$ Heteroaryl" means 2- or 3-furyl, 2- or 3-thienyl, or 2-, 3-, or 4-pyridinyl. "Substituted $C_{5-6}$ heteroaryl" means $C_{5-6}$ heteroaryl substituted in the manner described above for substituted phenyl.

"Salts" are described in the section entitled "Compounds of this invention".

An "amine-protecting group" is a group capable of protecting the glutamyl α-amine group of a compound of the first aspect of this invention or an intermediate thereto during the synthesis of that compound, and subsequently removable without affecting the remainder of the compound of the first aspect of this invention. Common such groups include tert-butoxycarbonyl and benzyloxycarbonyl, conveniently removable by acidolysis. Amine-protecting groups are well known in the field of organic synthesis and particularly peptide synthesis. Suitable such groups, and the conditions for their removal, are described in books such as *Synthesis of Peptides and Peptidomimetics, Workbench edition*, M. Goodman, ed., Georg Thieme Verlag, Stuttgart, Germany, 2004, and *Protective groups in organic synthesis*, 3 ed., T. W. Greene and P. G. M. Wuts, eds., John Wiley & Sons, Inc., New York, N.Y., U.S.A., 1999, and will be well known to a person of ordinary skill in the art.

A "therapeutically effective amount" means the amount that, when administered to a mammal, especially a human, for effecting treatment by one of the therapeutic methods, is sufficient to effect treatment for the condition that is the object of that therapeutic treatment. "Treating" or "treatment" of a condition in a mammal includes one or more of:

(1) inhibiting development of the condition, e.g., arresting its development, (2) relieving the condition, e.g., causing regression of or curing the condition, (3) preventing recurrence of the condition, and (4) palliating symptoms of the condition.

The Compounds of this Invention and their Preparation

The compounds of the first aspect of this invention are compounds of the formula

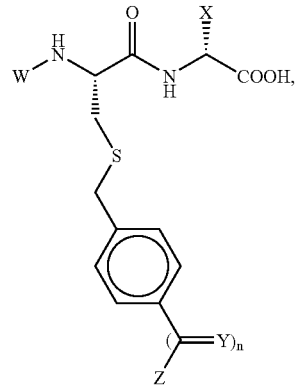

where:

n is 0 or 1;

W is L-γ-glutamyl or L-γ-glutamylglycyl;

X is optionally substituted $C_{5-6}$ cycloalkyl, optionally substituted $C_{5-6}$ heterocycloalkyl, optionally substituted phenyl, or optionally substituted $C_{5-6}$ heteroaryl;

Y is =O, =N—OH, or =N—O(optionally substituted $C_{1-3}$ alkyl); and

Z is optionally substituted phenyl or optionally substituted $C_{5-6}$ heteroaryl;

and their $C_{1-10}$ alkyl, phenyl-$C_{1-3}$ alkyl, or ($C_{5-6}$ heteroaryl)-$C_{1-3}$ alkyl mono- and di-esters;

and salts of the compounds and their mono- and di-esters.

Preferred compounds of the first aspect of this invention include those compounds having one or more of the following features:

1. W is L-γ-glutamyl;

2. X is cyclopentyl, cyclohexyl, furyl, thienyl, or pyridinyl, or optionally substituted phenyl; especially cyclohexyl or 3-thienyl, or phenyl optionally substituted with fluoro, chloro, cyano, methyl, hydroxy, or methoxy, especially where the phenyl is unsubstituted or has 1 substituent in the 4-position; such as phenyl, 4-chlorophenyl, and 4-hydroxyphenyl;

3A. n is 0; or 3B. n is 1, and Y is =O, =N—OH, or =N—OCH$_2$CH$_2$NH$_2$;

4. the Z—C(=Y)$_n$— substituent is in the 2- or 4-position of the phenyl group to which it is attached;

5. Z is pyridyl, or is optionally substituted phenyl;

6A. the compound is a diacid; or 6B. the compound is a diester, especially a $C_{1-6}$ alkyl diester, more especially a $C_{1-3}$ alkyl diester, particularly a diethyl ester.

Generally, a compound having a greater number of these features is preferred over a compound having a lesser number of these feature; in particular, addition of one of these features to a compound having less than all the features will generally result in a compound that is preferred over the compound without that feature.

Suitable salts (see Berge et al., *J. Pharm. Sci.*, 66:1 (1971) for a nonexclusive list) of the compounds of this invention are those formed when inorganic bases (e.g. sodium, potassium, and calcium hydroxide) or organic bases (e.g. ethanolamine, diethanolamine, triethanolamine, ethylenediamine, tromethamine, N-methylglucamine) react with the carboxyl groups, and those formed when inorganic acids (e.g hydrochloric, hydrobromic, sulfuric, nitric, and chlorosulfonic acids) or organic acids (e.g. acetic, propionic, oxalic, malic, maleic, malonic, fumaric, or tartaric acids, and alkane- or arenesulfonic acids such as methanesulfonic, ethanesulfonic, benzenesulfonic, substituted benzenesulfonic such as chlorobenzenesulfonic and toluenesulfonic, naphthalenesulfonic and substituted naphthalenesulfonic, naphthalenedisulfonic and substituted naphthalenedisulfonic, and camphorsulfonic acids) react to form acid addition salts of the amine groups, of the compounds. Such salts are preferably formed with pharmaceutically acceptable acids and bases. A suitable salt for the compounds is an acid addition salt, especially with an inorganic acid, such as the hydrochloride salt.

The preparation of the compounds of the first aspect of this invention by the process of this invention involves one of steps (a1) to (a4):

(a1) alkylating the cysteine sulfur atom of a tripeptide or tetrapeptide of the formula

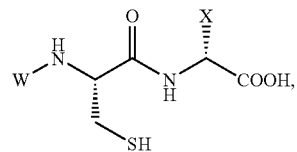

or its mono- or diester, typically with the glutamyl amine group $R^1$-protected, with a substituted benzyl group of the formula

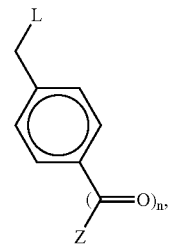

where L is a leaving group such as chlorine, bromine, or an optionally substituted $C_{1-6}$ alkane- or benzenesulfonate such as methane-, trifluoromethane-, benzene-, 4-toluene-, 4-nitrobenzene-, 4-chlorobenzene-, or 4-bromobenzenesulfonate, especially bromine; or (a2) coupling an optionally protected dipeptide or tripeptide of the formula

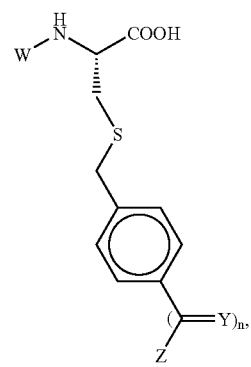

where if n is 1, Y is =O;

or its monoester at the glutamyl carboxylate, typically with the glutamyl amine group $R^1$-protected, with an amino acid of the formula

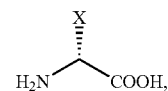

or its monoester; or (a3) coupling a dipeptide of the formula

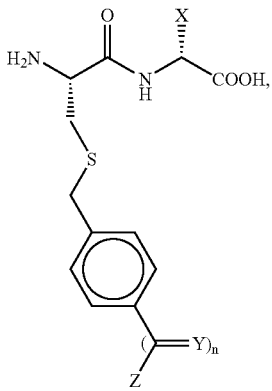

where if n is 1, Y is =O;

or its monoester, with an optionally protected L-γ-glutamic acid or L-γ-glutamylglycine, optionally esterified at the glutamyl α-carboxylate; or (a4) coupling a tripeptide or tetrapeptide of the formula

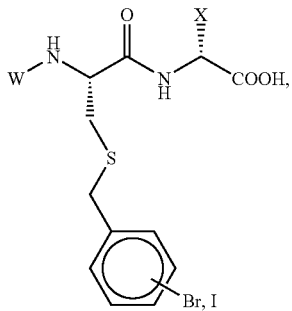

or its mono- or diester, with a Z-boronic acid to give a compound of the formula

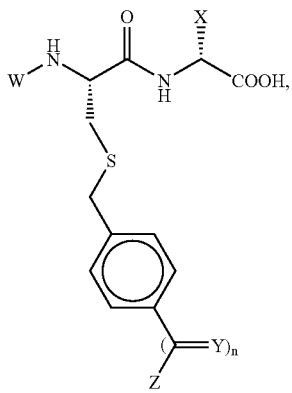

where n is 0, or its mono- or diester;

optionally followed by one or more of steps (b) to (e):

(b) if W is N-α-$R^1$-L-γ-glutamyl or N-α-$R^1$-L-γ-glutamylglycyl in the compound prepared in step (a), deprotecting the compound of the fourth aspect of this invention to give a compound of the first aspect of this invention;

(c) if n is 1, reacting a compound where Y is =O with hydroxylamine or an O-(optionally substituted $C_{1-3}$ alkyl) hydroxylamine to form a compound where =N—OH, or =N—O(optionally substituted $C_{1-3}$ alkyl);

(d1) if the compound is a diacid, forming a mono- or diester of the compound; or (d2) if the compound is a mono- or diester, de-esterifying the compound to prepare the diacid of the compound; and (e) forming a salt of the compound prepared in any of steps (a) to (e).

The starting materials for the process of step (a1) are tripeptides and tetrapeptides, optionally mono- or di-esterified, optionally protected at the glutamyl amine, and with the cysteine sulfur deprotected. These glutathione analogs are conveniently prepared by conventional methods of peptide synthesis well-known to persons of ordinary skill in the art.

The peptide synthesis may be performed using one of the many standard S-protecting groups, such as triphenylmethyl, and the resulting S-protected peptide then deprotected, for example by acidolysis. Typically, the S-protected peptide is dissolved in an acid that is strong enough to remove the acidolytically removable sulfur-protecting group but not strong enough to remove any amine-protecting group, optionally in the presence of a scavenger. Suitable such acids include trifluoroacetic acid and other strong acids such as trifluoromethanesulfonic acid, optionally in the presence of a cosolvent such as dichloromethane; suitable scavengers include aromatic ethers and sulfides such as anisole and thioanisole, phenols such as cresol, and, most efficiently, silanes including trialkylsilanes such as triethylsilane and triisopropylsilane and silane polymers such as poly(methylhydrosiloxane); and a particularly suitable deprotection reagent is trifluoroacetic acid in the presence of poly(methylhydrosiloxane). The S-deprotected peptide can be isolated from the reaction mixture by addition of an anti-solvent, for example an aprotic non-polar solvent such as a hydrocarbon or an ether.

A convenient preparation of N-α-(benzyloxycarbonyl)-L-γ-glutamyl-L-cysteinyl-D-phenylglycine, the starting peptide for a number of the compounds of this invention, using the readily available starting materials N-α-(benzyloxycarbonyl)-L-γ-glutamic acid α-benzyl ester, S-triphenylmethyl-L-cysteine, and D-phenylglycine, is as follows. N-α-(benzyloxycarbonyl)-L-γ-glutamic acid α-benzyl ester is activated as the N-hydroxysuccinimide ester by reaction with N-hydroxysuccinimide and dicyclohexyl-carbodiimide in anhydrous 1,4-dioxane. The N-α-(benzyloxycarbonyl)-L-γ-glutamic acid α-benzyl ester γ-N-hydroxysuccinimide ester is dissolved in anhydrous tetrahydrofuran, and added to a solution of S-(triphenylmethyl)-L-cysteine and triethylamine in water to give O-α-benzyl-N-α-(benzyloxycarbonyl)-L-γ-glutamyl-S-(triphenylmethyl)-L-cysteine. This is activated as the N-hydroxysuccinimide ester and coupled with D-phenylglycine in the same way as for the coupling between the γ-glutamine and cysteine to give O-α-benzyl-N-α-(benzyloxycarbonyl)-L-γ-glutamyl-S-(triphenylmethyl)-L-cysteinyl-D-phenylglycine.

Similar methods but using different activating groups or methods to activate the γ-carboxyl group of the glutamic acid and/or the cysteine carboxyl group for the coupling may also be used; as may methods in which the cysteine-phenylglycine coupling is performed first, followed by coupling of the resulting S-(triphenylmethyl)-L-cysteinyl-D-phenylglycine with the N-α-(benzyloxycarbonyl)-L-γ-glutamic acid α-benzyl ester. Other protection of the α-carboxyl group of the N-α-(benzyloxycarbonyl)-L-γ-glutamic acid also may be used provided the α-carboxyl group ultimately can be deprotected while leaving the remainder of the N-α-(benzyloxycarbonyl)-L-γ-glutamyl-S-(triphenylmethyl)-L-cysteinyl-D-phenylglycine molecule intact. The O-α-benzyl-N-α-(benzyloxycarbonyl)-L-γ-glutamyl-S-(triphenylmethyl)-L-cysteinyl-D-phenylglycine is dissolved in a lower alcohol (e.g. methanol) and the benzyl ester is removed by hydrolysis with aqueous base (e.g. 1 M NaOH), followed by acidification to allow isolation of the N-α-(benzyloxycarbonyl)-L-γ-glutamyl-S-(triphenylmethyl)-L-cysteinyl-D-phenylglycine as an acid addition salt. The cysteine sulfur of the N-α-(benzyloxycarbonyl)-L-γ-glutamyl-S-(triphenylmethyl)-L-cysteinyl-D-phenylglycine is then deprotected by reaction with trifluoroacetic acid and poly(methylhydrosiloxane) in toluene, and the N-α-(benzyloxycarbonyl)-L-γ-glutamyl-L-cysteinyl-D-phenylglycine can be precipitated with heptane/methyl tert-butyl ether.

Other peptides may easily be prepared by similar methods, starting from the amino acids, or from dipeptides if available. Many of the amino acids of the formula

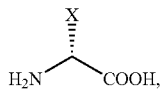

such as D-phenylglycine, D-(4-chlorophenyl)glycine, D-(4-hydroxypheny)glycine, D-(3-thienyl)glycine, D-cyclohexylglycine, are commercially available in resolved form, and in some cases as the esters. Others are available in racemic form, but may be resolved by any of the methods known for the resolution of amino acids.

Then, in step (a1) the thiolate anion of the S-deprotected peptide is alkylated with a substituted benzyl group of the formula

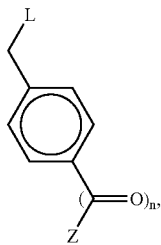

where L is a is a leaving group such as chlorine, bromine, or an optionally substituted $C_{1-6}$ alkane- or benzenesulfonate such as a methane-, trifluoromethane-, benzene-, 4-toluene-, 4-nitrobenzene-, 4-chlorobenzene-, or 4-bromobenzene-sulfonate, especially bromine to prepare the appropriately S-alkylated peptide. This is conveniently done when the glutamyl amine is protected, to minimize side reactions, but can be done even when the amine is unprotected.

Typically, the S-deprotected peptide is dissolved in a solution of a strong base (e.g. an alkali metal or alkaline earth metal hydroxide, carbonate, bicarbonate, phosphate, or alkoxide, or ammonium hydroxide; or an organic amine base such as tetramethylguanidine, 1,8-diazabicyclo[5.4.0]undec-7-ene (DBU), and the like) in a suitable solvent (e.g. a $C_{1-6}$ alkanol, a diol such as 1,2-ethanediol or 1,3-propanediol, an ether such as 2-methoxyethanol, 1,2-dimethoxyethane, or tetrahydrofuran, and the like) to form the thiolate anion, the substituted benzyl group is added (typically in excess), and the reaction mixture is held at an appropriate temperature and time until completion. Convenient reaction conditions are the use of 20% tetrahydrofuran in water and an approximately ten-fold excess of sodium bicarbonate.

The peptide may be prepared as a diacid (though this may involve intermediate protection of the glutamyl α-carboxyl as well as the amine) or as a mono- or diester, depending on the state of the starting amino acids. If the peptide is prepared as a diacid, it may be mono- or di-esterified (typically while amine-protected) before alkylation of the cysteine sulfur atom, and the esterification conditions will typically be similar to those that may be used for esterification of a compound of the first aspect of this invention.

In steps (a2) and (a3), the thiolate anion of an optionally amine-protected cysteine is first alkylated with a substituted benzyl group of the formula

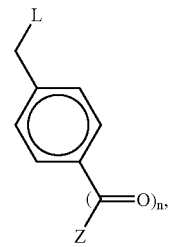

to form the central amino acid of the tripeptide or tetrapeptide of the first aspect of this invention; and the peptide is then assembled by conventional methods of peptide synthesis.

The alkylation of the cysteine may be performed by similar methods to those used for the alkylation of the tripeptide or tetrapeptide above; and the coupling of the various amino acids to give the resulting peptide that is a compound of the first or fourth aspects of this invention may also be performed by similar methods to those discussed above.

In step (a4), an S-[(halophenyl)methyl]-cysteine-containing tripeptide or tetrapeptide [which has been synthesized by any convenient method, e.g. by alkylation of the S-unprotected peptide in the manner described for step (a1) or by alkylation of cysteine followed by coupling to form the peptide in the manner described above for steps (a2) and (a3)] is coupled in a Suzuki coupling with a boronic acid of the formula Z—B(OH)$_2$.

In optional step (b), the $R^1$-protected amine group of a compound of the fourth aspect of this invention is deprotected to prepare a compound of the first aspect of this invention by any method suitable for removal of the amine-protecting group that does not also affect the remainder of the molecule, typically by acidolysis using a strong acid, such as trifluoroacetic acid, optionally in the presence of dichloromethane.

In optional step (c), the compound of the first aspect of this invention where n is 1 and Y is =O is reacted with hydroxylamine or an O-(optionally substituted $C_{1-3}$ alkyl)

hydroxylamine to form a compound where =N—OH or =N—O(optionally substituted $C_{1-3}$ alkyl). The reaction is typically carried out by reaction with the hydroxylamine in an aqueous solution (optionally also containing a water-miscible organic solvent such as tetrahydrofuran) in the presence of a base.

In optional steps (d1) and (d2), the compound of the first aspect of this invention is esterified (if an ester is desired), or de-esterified (if the diacid is desired). These esterifications or de-esterifications are conventional and may be carried out by any of the methods well known to persons of ordinary skill in the art; in particular, a convenient esterification technique involves the reaction of the diacid compound of the first aspect of this invention with the alcohol that produces the desired ester, using that alcohol as solvent, in the presence of a halosilane such as chlorotrimethylsilane at temperatures between room temperature and the boiling temperature of the alcohol.

In optional step (e), a salt of the compound of the first aspect of this invention is formed. This will typically be an acid addition salt (see the definition of "salts" above). Conveniently, this is done immediately after the compound of the first aspect of this invention is formed; and may be accomplished by addition of a solvent that will become an anti-solvent for the salt, such as an aprotic solvent, e.g. a hydrocarbon or halogenated hydrocarbon such as dichloromethane, followed by addition of the acid chosen to form the salt, especially in the form of the anhydrous acid alone or in an aprotic solvent, e.g. hydrogen chloride gas. Further anti-solvent for the salt, e.g. ethers such as diethyl ether, methyl tert-butyl ether, and tetrahydrofuran, especially methyl tert-butyl ether, may be added if necessary or desired.

A person of ordinary skill in the art will have no difficulty, considering that skill and this disclosure (including the Examples), in preparing compounds of the fourth and first aspects of this invention.

Uses of the Compounds and Process

The compounds of the first aspect of this invention (especially in the acid form) are very potent inhibitors, typically selective inhibitors, of GST P1-1. They are also active in enhancing the differentiation of HL-60 cells in intro, and one has been shown to enhance granulocyte/monocyte colony formation from murine bone marrow cells ex vivo. The compounds are therefore expected to act therapeutically in humans to: potentiate the cytotoxic effects of chemotherapeutic agents in tumor cells (because GST, especially GST P1-1, which is elevated in many tumor tissues, is implicated in the resistance of tumor cells to chemotherapeutic agents; so that a GST inhibitor will reduce the ability of the tumor cells to clear the chemotherapeutic agent), selectively exert cytotoxicity in tumor cells (again because of GST isoenzyme inhibition), elevate the production of GM progenitors in bone marrow, stimulate the differentiation of bone marrow, mitigate the myelosuppressive effects of chemotherapeutic agents, and modulate hematopoiesis in bone marrow.

The compounds of the fourth aspect of this invention and the process of the fifth aspect of this invention are useful in the preparation of compounds of the first aspect of this invention.

The second aspect of this invention is pharmaceutical compositions comprising a compound of the first aspect of this invention, optionally also including an excipient, such as a pharmaceutically acceptable excipient.

The third aspect of this invention is therapeutic methods involving administering the compounds of the first aspect of this invention or the pharmaceutical compositions of the second aspect of this invention, typically in a therapeutically effective amount, and the use of these compounds for one or more of: potentiating the cytotoxic effects of chemotherapeutic agents in tumor cells, selectively exerting toxicity in tumor cells, elevating the production of GM progenitors in bone marrow, stimulating the differentiation of bone marrow, mitigating the myelosuppressive effects of chemotherapeutic agents, and modulating hematopoiesis in bone marrow.

The compounds may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Pharmaceutical compositions containing these compounds may optionally be liposomal formulations, emulsions, formulations designed to administer the drug across mucosal membranes or transdermal formulations. Suitable formulations for each of these methods of administration may be found, for example, in *Remington: The Science and Practice of Pharmacy*, 20 ed., A. Gennaro, ed., Lippincott Williams & Wilkins, Philadelphia, Pa., U.S.A., 2003. Typical compositions will be either oral or solutions for intravenous infusion and will contain the compound and typically will also contain one or more pharmaceutically acceptable excipients. Typical dosage forms will be tablets, solutions for intravenous infusion, lyophilized powders for reconstitution as solutions for intravenous infusion, and liposomal formulations and lyophilized liposomal formulations also for intravenous administration.

A therapeutically effective amount of a compound of the first aspect of this invention is about 10–2000 mg/m² body surface area, especially 50–1000 mg/m². Administration may be at 1–35 day intervals; for example, about 250–1000 mg/m² at 1–5 week intervals, especially at 1, 2, 3, or 4 week intervals, or at higher frequencies including as frequently as once/day for several (e.g. 5 or 7) days, with the administration repeated every 2, 3, or 4 weeks, or constant infusion for a period of 6–72 hours, also with the administration repeated every 2, 3, or 4 weeks. A typical regimen may involve administration once/day for five days every three weeks.

PREPARATIONS AND EXAMPLES

The following examples show the preparations of useful intermediates and the syntheses of the compounds of this invention by the process of this invention, and the utility of the compounds of the first aspect of this invention as therapeutic agents.

Preparations 1 and 2 describe preparations of reagents for S-alkylation of cysteine or the cysteine of the tripeptides and tetrapeptides. For convenience, the reagents are named as derivatives of benzyl bromide (α-bromotoluene).

Preparation 1

Preparation of 4-(2-pyridyl)benzyl bromide 4-(2-Pyridyl)toluene, 2 mL (1.98 g, 11.7 mmol), N-bromosuccinimide (NBS), 2.5 g (14.0 mmol), and α,α'-azobis(isobutyronitrile)(AIBN), 23 mg (0.14 mmol) were suspended in 35 mL tetrachloromethane, and refluxed for 24 hours. The product was filtered, and the solvent removed from the filtrate by rotary evaporation. Equal amounts of chloroform and water were added and the product extracted. The chloroform layer was separated and dried, and the solvent removed. 4-(2-Pyridyl)benzyl bromide, 2 g, was obtained as a sticky yellow solid.

4'-(4-carboxyphenyl)benzyl bromide was prepared from 4'-methyl-4-biphenylcarboxylic acid; 4'-(4-(methoxycarbonyl)benzyl bromide was prepared from methyl 4'-methyl-4-biphenylcarboxylate (obtained from the carboxylic acid by esterification with methanol and chlorotrimethylsilane), and 4-(benzoyl)benzyl bromide was prepared from 4-methylbenzophenone, by this method.

Preparation 2

Preparation of 4-(2-methoxyphenyl)benzyl bromide 4-bromotoluene, 171 mg (1 mmol), 2-methoxyphenylboronic acid, 152 mg (1 mmol), palladium diacetate, 1 mg (4 µmol), N-butylammonium bromide, 322 mg (1 mmol), and 2 M aqueous $Na_2CO_3$, 1.9 mL (3.8 mmol), were placed in a microwaveable pressure vial and heated to 150 C for 5 minutes. After cooling to room temperature, the product was poured into a separatory funnel and 30 mL each of water and diethyl ether were added. After extraction, the layers were separated and the aqueous layer washed with another 30 mL diethyl ether. The ether extracts were combined, dried over $MgSO_4$, and the solvent removed by rotary evaporation under vacuum. 2-methoxy-4'-methylbiphenyl, 160 mg (81% yield) was obtained as a solid product, 95% purity by NMR.

2-methoxy-4'-methylbiphenyl, 160 mg (0.81 mmol), NBS, 158 mg (0.91 mmol), and AIBN, 1 mg (0.006 mmol) were suspended in 7 mL tetrachloromethane, and refluxed for 24 hours. The product was filtered, and the solvent removed from the filtrate by rotary evaporation. Equal amounts of diethyl ether and water were added and the product extracted. The ether layer was separated and dried over $MgSO_4$, filtered, and the solvent removed. 4-(2-Methoxyphenyl)benzyl bromide, 128 mg, was obtained as an oil.

4'-(4-cyanophenyl)benzyl bromide was prepared from 4-cyanophenylboronic acid, and 4'-[3-(trifluoromethyl)phenyl]benzyl bromide was prepared from 3-(trifluoromethyl) phenylboronic acid, by this method.

Other benzyl bromides substituted with optionally substituted phenyl, optionally substituted $C_{5-6}$ heteroaryl, optionally substituted benzoyl, or (optionally substituted $C_{5-6}$ heteroaryl)carbonyl may readily be prepared by the methods of these preparations.

Preparation 3 describes the preparation of an S-alkylated cysteine.

Preparation 3

Preparation of N-α-(tert-butoxycarbonyl)-S-(4-biphenylylmethyl)-L-cysteine

N-α-(tert-Butoxycarbonyl)-L-cysteine, 1.0 g (4.52 mmol), is dissolved in a mixture of 9 mL tetrahydrofuran and 9 mL 1 M aqueous NaOH which had been degassed by bubbling argon through it. A solution of 4-(bromomethyl) biphenyl, 1,12 g (4.53 mmol), in 5 mL tetrahydrofuran (THF) was added and the solution stirred under argon bubbling for 8 hours at room temperature. The THF was removed by rotary evaporation under vacuum and the residue diluted with water and washed with diethyl ether. The aqueous phase was acidified to pH 3 with 6 M aqueous HCl, and extracted three times with ethyl acetate. The combined organic extracts were washed with water, saturated aqueous $NaHCO_3$, water, and brine, and then dried and concentrated to give 1.44 g N-α-(tert-butoxycarbonyl)-5-(4-biphenylylmethyl)-L-cysteine (82% yield) as a white solid.

Other (optionally protected) S-alkylated cysteines may be readily prepared by the method of this preparation.

Synthesis Example 1

Synthesis of L-γ-glutamyl-S-[(4-biphenylyl)methyl]-L-cysteinyl-D-phenylglycine [illustrating steps (a1), (b), and (e)]

L-γ-glutamyl-S-[(4-biphenylyl)methyl]-L-cysteinyl-D-phenylglycine, 1A, as the hydrochloride salt, was prepared from 330 mg N-α-(benzyloxycarbonyl)-L-γ-glutamyl-L-cysteinyl-D-phenylglycine by dissolving the amine-protected peptide in acetonitrile/water, adding an approximate 10-fold excess of sodium bicarbonate, and adding a slight excess of 4-(bromomethyl)biphenyl, then maintaining the reaction under nitrogen until completion. The reaction mixture was diluted with water, washed with diethyl ether, and the aqueous phase separated and acidified to pH 2–3 with hydrochloric acid, then extracted with ethyl acetate. The organic phase was dried over anhydrous $MgSO_4$, filtered, and the volume reduced to give N-α-(benzyloxycarbonyl)-L-γ-glutamyl-S-[(4-biphenylyl)methyl)-L-cysteinyl-D-phenylglycine. The amine-protected sulfide, approx. 300 mg, was dissolved in 2 mL 95:5 trifluoroacetic acid(TFA):dichloromethane with 1 drop water, and stirred at 45° C. overnight, and purified by preparative HPLC to give L-γ-glutamyl-S-[(4-biphenylyl)methyl)-L-cysteinyl-D-phenylglycine. The L-γ-glutamyl-S-[(4-biphenylyl)methyl]-L-cysteinyl-D-phenylglycine was isolated as the hydrochloride salt.

Compounds such as L-γ-glutamyl-S-{[4-(2-pyridyl)phenyl]methyl}-L-cysteinyl-D-phenylglycine, compound 8A, and L-γ-glutamyl-S-[(4-benzoylphenyl)methyl]-L-cysteinyl-D-phenylglycine, compound 9A, were prepared by similar methods.

Other tripeptides and tetrapeptides of the first aspect of this invention, including compounds that are mono- and diesters, may readily be prepared by similar methods.

Synthesis Example 2

Synthesis of L-γ-glutamyl-S-[(4-biphenylyl)methyl]-L-cysteinyl-D-phenylglycine diethyl ester [illustrating steps (d1) and (e)]

L-γ-glutamyl-S-[(4-biphenylyl)methyl]-L-cysteinyl-D-phenylglycine diethyl ester, 1B, as the hydrochloride salt, was prepared from L-γ-glutamyl-5-[(4-biphenylyl)methyl]-L-cysteinyl-D-phenylglycine, 30 mg, by esterification with ethanol and chlorotrimethylsilane, giving L-γ-glutamyl-S-[(4-biphenylyl)methyl)-L-cysteinyl-D-phenylglycine diethyl ester, exact mass 605, MS (m/z) 606 (M+H). The L-γ-glutamyl-S-[(4-biphenylyl)methyl]-L-cysteinyl-D-phenylglycine diethyl ester was isolated as the hydrochloride salt.

Compounds such as L-γ-glutamyl-5-{[4-(2-pyridyl)phenyl]methyl}-L-cysteinyl-D-phenylglycine diethyl ester, compound 8B, and L-γ-glutamyl-S-[(4-benzoylphenyl)methyl]-L-cysteinyl-D-phenylglycine diethyl ester, compound 9B, were prepared by similar methods. Other esters, particularly diesters, of the compounds of the first aspect of this invention may readily be prepared by similar methods.

Synthesis Example 3

Synthesis of L-γ-glutamyl-5-[(4-biphenylyl)methyl]-L-cysteinyl-D-cyclohexylglycine [illustrating steps (a3), (b), and (e)]

D-Cyclohexylglycine ethyl ester was prepared from D-cyclohexylglycine, 500 mg (3.1 mmol), by suspending the acid in 15 mL ethanol, adding chlorotrimethylsilane, 2.02 mL (5 equivalents), and heating the mixture at 50° C. for 18 hours. The volatile components were removed under vacuum and the residue dissolved in ethyl acetate, washed with aqueous NaHCO₃ and twice with brine, dried over MgSO₄, filtered, and evaporated to give 401 mg D-Cyclohexylglycine ethyl ester as an oily solid.

N-α-(tert-butoxycarbonyl)-S-(4-biphenylylmethyl)-L-cysteine, 588 mg (1.9 mmol), was dissolved in 5 mL dimethylformamide (DMF), and O-benzotriazole-N,N,N',N'-tetramethyluronium hexafluorophosphate (HBTU), 860 mg (1.2 equiv.), and di(isopropyl)ethylamine, 990 μL (3 equiv.), were added. After 3 minutes, D-cyclohexylglycine ethyl ester, 360 mg (1 equiv.), dissolved in 4 mL DMF, was added, and the mixture stirred at room temperature for 2 hours, then the crude N-α-(tert-butoxycarbonyl)-S-(4-biphenylylmethyl)-L-cysteinyl-D-cyclohexylglycine ethyl ester isolated. The dipeptide was dissolved in 10 mL 20% TFA/dichloromethane, and stirred at room temperature for 2 hours, then the crude product isolated by removal of volatiles under vacuum. The crude 5-(4-biphenylylmethyl)-L-cysteinyl-D-cyclohexylglycine trifluoroacetate may be used directly in the next step, or may be further processed.

N-α-(tert-butoxycarbonyl)-O-α-tert-butyl-L-γ-glutamine was dissolved in 2 mL DMF, and HBTU, 174 mg (1.2 equiv.), and di(isopropyl)ethylamine, 330 μL (5 equiv.), were added. After 5 minutes, crude S-(4-biphenylylmethyl)-L-cysteinyl-D-cyclohexylglycine trifluoroacetate, 200 mg (0.38 mmol), dissolved in 2 mL DMF, was added, and the mixture stirred at room temperature for 2 hours. The mixture was poured into 0.1 N aqueous citric acid, and extracted with ethyl acetate. The organic layer was washed four times with brine, dried over MgSO₄, and the volatiles evaporated to give N-α-(tert-butoxycarbonyl)-O-α-tert-butyl-L-γ-glutamyl-S-(4-biphenylylmethyl)-L-cysteinyl-D-cyclohexylglycine as a brown oil. This was dissolved in 10 mL 20% TFA/dichloromethane and stirred at room temperature for 24 hours. The volatiles were removed under vacuum and the product purified by reverse phase HPLC, then the L-γ-glutamyl-S-(4-biphenylylmethyl)-L-cysteinyl-D-cyclohexylglycine, compound 12A, isolated as the hydrochloride salt, 47 mg.

L-γ-glutamyl-5-(4-biphenylylmethyl)-L-cysteinyl-D-(4-chlotophenyl)glycine, compound 11A, was prepared as the hydrochloride salt by a similar method.

Synthesis Example 4

Synthesis of L-γ-glutamyl-S-({4-[(2-aminoethoxyimino)(phenyl)methyl]-phenyl}methyl)-L-cysteinyl-D-phenylglycine [illustrating step (c)]

L-γ-Glutamyl-S-({4-[(2-aminoethoxyimino)(phenyl)methyl]phenyl}methyl)-L-cysteinyl-D-phenylglycine, compound 10A, was prepared by treating L-γ-glutamyl-S-[(4-benzoylphenyl)methyl]-L-cysteinyl-D-phenylglycine, 108 mg (0.18 mmol), with O-(2-aminoethyl)hydroxylamine dihydrochloride, 26 mg (0.18 mmol), in 5 mL water, 5 mL THF, and 10 mL 0.5 M sodium phosphate at pH 4.5. The mixture was heated at 50° C. overnight, and the product purified by HPLC with hydrochloric acid buffets, isolating approx. 45 mg each of the two isomers (at the oxime nitrogen) of L-γ-glutamyl-S-({4-[(2-aminoethoxyimino)(phenyl)methyl]phenyl}methyl)-L-cysteinyl-D-phenylglycine as the hydrochloride salts.

L-γ-Glutamyl-S-({4-[(2-aminoethoxyimino) (phenyl)methyl]phenyl}methyl)-L-cysteinyl-D-phenylglycine diethyl ester, compound 10B, was prepared by the same method starting from L-γ-glutamyl-S-[(4-benzoylphenyl)methyl]-L-cysteinyl-D-phenylglycine diethyl ester, also giving two isomers.

Representative compounds of the first aspect of this invention are given in Table 1 below:

TABLE 1

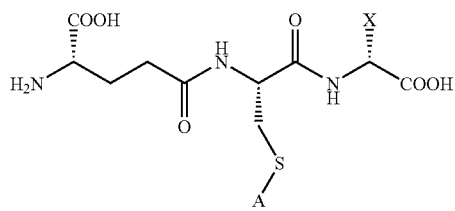

Diacid compounds of the first aspect of this invention

| Compound No. | X | A | Exact Mass (M) | MS (m/z) |
|---|---|---|---|---|
| TLK117 | phenyl | benzyl | | |
| TLK137 | phenyl | 4-chlorobenzyl | | |

TABLE 1-continued
Diacid compounds of the first aspect of this invention
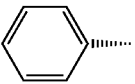
| Compound No. | X | A | Exact Mass (M) | MS (m/z) |
|---|---|---|---|---|
| 1A | 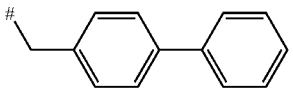 | 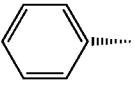 | 549 | 550 (M + H) |
| 2A | 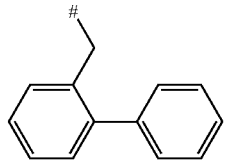 | 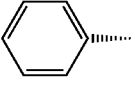 | 549 | 548 (M − H) |
| 3A | 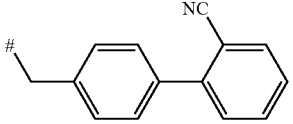 | 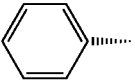 | 574 | 575 (M + H) |
| 4A | 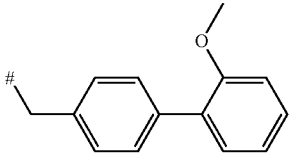 | 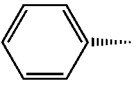 | 579 | 580 (M + H) |
| 5A | 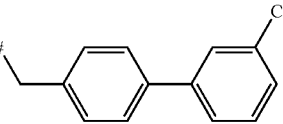 | 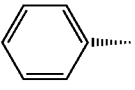 | 617 | 618 (M + H) |
| 6A | 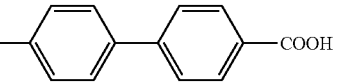 | 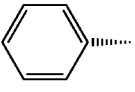 | 593 | 592 (M − H) |
| 7A | 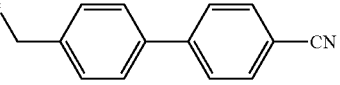 | 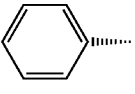 | 574 | 575 (M + H) |
| 8A | 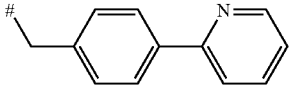 | 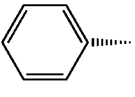 | 550 | 549 (M − H) |
| 9A | 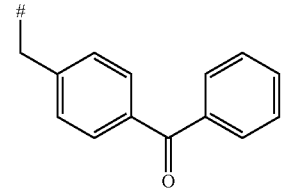 |  | 577 | 578 (M + H) |

TABLE 1-continued

Diacid compounds of the first aspect of this invention

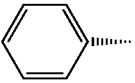

| Compound No. | X | A | Exact Mass (M) | MS (m/z) |
|---|---|---|---|---|
| 10A | 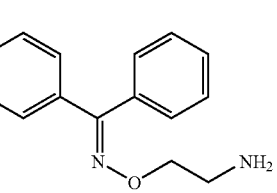 | 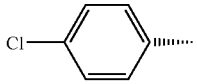 | 635 | 636 (M + H) |
| 11A | 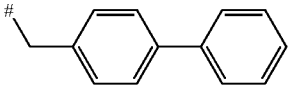 | 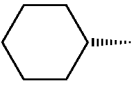 | 583 | 585 (M + 2) |
| 12A | 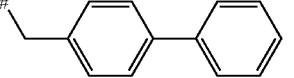 | 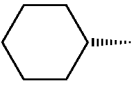 | 555 | 554 (M − H) | denotes the point of attachment of A to the cysteine sulfur of the rest of the compound The diethyl esters 1B to 12B of compounds 1A to 12A were prepared by one of the methods discussed above, except that compound 9B was not prepared; and analyzed by mass spectrometry, with each compound giving a mass peak (M/z) corresponding to its mass, typically M+H with positive ionization, or M−H with negative ionization.

Compound 10A and its diethyl ester 10B are isolated as the dihydrochloride salts, and exist as two isomers at the oxime nitrogen. The isomers have been separated.

Other compounds of this invention may be similarly prepared, using methods well known to a person of ordinary skill in the art having regard to that skill and this disclosure.

In vitro assay examples.

These examples illustrate the effects of compounds of this invention (and one or other of the comparator compounds TLK117 and TLK199, and TLK137) in predictive in vitro assays.

Recombinant human GST P1-1, A1-1, and M1-1 isoenzymes, and rabbit polyclonal anti-human GSTπ antibody were obtained from EMD Biosciences, Inc., San Diego, Calif., U.S.A. Mouse monoclonal anti-human GSTπ antibody was obtained from was obtained from Dakoctyomation, Inc., Carpinteria, California, U.S.A. IRDye800 conjugated, affinity purified goat anti-rabbit IgG antibody was obtained from Rockland Immunochemicals, Inc., Gilbertsville, Pa., U.S.A. The human cancer cell line HL-60 (promyeloid myelocytic leukemia) was obtained from the National Cancer Institute, Bethesda, Md., U.S.A. RPMI 1640 medium and Iscove's Modified Dulbecco's Medium (IMDM) were obtained from Invitrogen, Inc., Carlsbad, Calif., U.S.A. The CellTiter-Glo™ assay kit was obtained from Promega Corporation, Madison, Wis., U.S.A., and was used in accordance with manufacturer's directions. Phycoerythrin-conjugated anti-CD11b antibody and phycoerythrin-conjugated isotype control antibody were obtained from BD Biosciences, Inc., San Jose, Calif., U.S.A. MethoCult™ M3234 methylcellulose medium (2.5% methylcellulose in IMDM, supplemented with fetal bovine serum, bovine serum albumin, rh insulin, h transferrin, 2-mercaptoethanol, and L-glutamine) was obtained from StemCell Technologies, Inc., Vancouver, Canada, and was diluted (to 1% methylcellulose concentration) in accordance with the manufacturer's directions.

In vitro Example 1. Inhibition of glutathione S-transferase isoenzymes. This example illustrates the effect of compounds of this as inhibitors of the glutathione S-transferase isoenzymes GST P1-1, A1-1, and M1-1, in vitro. Inhibition of GST P1-1 is considered predictive of efficacy in the therapeutic methods of the third aspect of this invention, because TLK199 (the diethyl ester of TLK117 tested in these assays) has shown myelostimulant activity in humans and chemopotentiation activity in an animal model.

Recombinant human GST P1-1, A1-1, and M1-1 isoenzymes were used at final concentrations of 0.02, 0.011, and 0.0083 units/mL, respectively [1 unit is the amount of enzyme that will conjugate 1 μmol of 1-chloro-2,4-dinitrobenzene (CDNB) to reduced glutathione (GSH) per minute at 20° C. and pH 6.5], in assay buffer (100 mM $KH_2PO_4/K_2HPO_4$, 0.1 mM EDTA, pH 6.5 in water). GSH was prepared as a 100 mM stock solution in water, and CDNB as a 100 mM stock solution in ethanol, and both were diluted with assay buffer to the appropriate concentration (to achieve a final concentration of $2×K_m$ for the isoenzyme being evaluated). The test compounds (diacids, compounds 1A to 12A and TLK117) were dissolved in dimethyl sulfoxide (DMSO) and diluted with DMSO to the appropriate concentration for the assay (8 concentrations over range with midpoint near expected $IC_{50}$). For each assay, the test compound and GSH were added to the isoenzyme. Immediately after the addition of CDNB solution to the isoenzyme/compound/GSH solution, the absorbance at 340 nm was recorded continuously for 5 min on a SpectraMax plate reader (Molecular Devices, Inc., Sunnyvale, Calif., U.S.A.). The GST inhibitory activity of each compound was calculated from the slopes of the absorbance/time curves at the various concentrations of test compound. All assays were conducted in duplicate wells, with DMSO control, with the final DMSO concentration maintained at 2%. Results of these assays are given in Table 2 below.

In vitro Example 2. Cytotoxicity in HL-60 cells. This example illustrates the cytotoxicity of compounds of this invention against the HL-60 human leukemia cell line in vitro.

Log-phase cells were seeded in 96-well plates at 1500 cells/well in 150 µL RPMI 1640 medium supplemented with 10% fetal bovine serum (FBS) and 1% L-glutamine, and incubated at 37° C. under air/5% $CO_2$ for 4–5 hours. The test compounds (diethyl esters, compounds 1B to 12B and TLK199) were dissolved and serially diluted in DMSO (8 concentrations over range with midpoint near expected $CC_{50}$). After a further 1:50 dilution in the supplemented RPMI 1640 medium, 50 µL of the diluted compounds were added to achieve a final DMSO concentration of 0.5%. The cells were then incubated for 72 hours (approximately three doubling times). The cells were then harvested by centrifugation (1200 rpm for 5 min at 20° C.), and 100 µL of the culture supernatant was removed and replaced by the same volume of the CellTiter-Glo reagent. After incubation for 10 minutes at room temperature with constant mixing, the plate was read with a luminometer, with the number of live cells being proportional to the observed luminescence. All assays were conducted in triplicate wells, with DMSO solvent control. The $CC_{50}$ (concentration that causes 50% growth inhibition) was calculated from the luminescence/concentration curve. Results of this assays are given in Table 2 below.

In vitro example 3. GSTπ immunoprecipitation assay. This example illustrates the beneficial effects of compounds of this invention in causing GSTπ immunoprecipitation. These results are considered predictive of efficacy in the therapeutic methods of the third aspect of this invention, because TLK199 (the diethyl ester of TLK117 tested in these assays) has shown myelostimulant activity in humans and chemopotentiation activity in an animal model.

HL60 cells were seeded at $6\times10^5$ cells/mL in 20 mL RPMI-1640 medium supplemented with 10% fetal bovine serum, 1 mM glutamine and 20 µM gentamycin in a T75 flask and cultured overnight in 5% $CO_2$ atmosphere at 37° C. The cells were treated with 0.1% DMSO or 20 µM of the test compounds (diethyl esters, compounds 1B to 12B and TLK199) in culture medium containing 0.1% DMSO for 2 hours. Following the treatment, the cells were collected by centrifugation and washed twice with phosphate-buffered saline. The cell pellets were resuspended in 1 mL lysis buffer (50 mM Tris, pH 8.0, 120 mM NaCl, 0.5% NP-40 surfactant, 100 mM NaF; to which protease and phosphatase inhibitors (Roche Diagnostics, Indianapolis, Ind., U.S.A.) had been added before use) and incubated with gentle agitation for 30 minutes at 4° C. The cell lysates were cleared by centrifugation at 13,000 rpm for 10 minutes to remove cell debris. For immunoprecipitation, 2.1 µg of mouse monoclonal anti-human GSTπ antibody was added to 500 µL cell lysate of 1 mg/mL total protein. Following overnight incubation at 4° C., 30 µL of Protein A/G agarose beads (Pierce, Rockford, Ill.) were added to the mixture and incubated for 1 hour at 4° C. The beads were then collected by centrifugation, washed three times in lysis buffer, and resuspended in 10 µL non-reducing lithium dodecyl sulfate sample buffer (Invitrogen, Carlsbad, Calif., U.S.A.). The suspended samples were heated at 95° C. for 5 minutes and subjected to SDS-PAGE on a 4–12% gel, followed by Western blot analysis using rabbit polyclonal anti-human GSTπ antibody followed by IRDye 800 conjugated, affinity purified goat anti-rabbit IgG antibody. GSTπ protein bands were visualized and band intensity quantified on Odyssey infrared scanner (Li-Cor, Lincoln, Nebr., U.S.A.). The band intensity from a compound treatment was compared to its corresponding DMSO control and expressed as percent inhibition. The results are shown in Table 2 below.

TABLE 2

GST isoenzyme inhibition by diacid compounds of this invention, and HL-60 cytotoxicity and GSTπ immunoprecipitation of diethyl ester compounds of this invention (*triethyl ester, including esterification at the biphenyl carboxylate, for compound 6).

| Compound | GST P1-1 $IC_{50}$, nM | GST A1-1 $IC_{50}$, µM | GST M1-1 $IC_{50}$, µM | HL-60 $CC_{50}$, µM | GSTπ inhibition, % |
|---|---|---|---|---|---|
| TLK117 | 409 | 17 | 70 | 16 | 90 |
| TLK137 | 52 | 10 | 6.5 | 10 | NM |
| 1 | 7 | 1.2 | 7.7 | 4.1 | 14 |
| 2 | 12 | 0.8 | 6.2 | 7.9 | 93 |
| 3 | 3 | 0.7 | 26 | 12 | 89 |
| 4 | 4 | 0.5 | 1.4 | 9.8 | NM |
| 5 | 3 | 1.1 | 3.6 | 4.4 | NM |
| 6 | 12 | 3.9 | 15 | 4.5* | NM |
| 7 | 19 | 1.0 | 2.2 | | |
| 8 | 13 | 7.7 | 52 | 7.2 | 100 |
| 9 | 9 | 2.9 | 17 | 11 | NM |
| 10 (isomer 1) | 4 | 120 | 95 | 21 | NM |
| 10 (isomer 2) | 22 | 160 | 130 | 9.9 | NM |
| 11 | 12 | NM | NM | 4.6 | 32 |
| 12 | 1.3 | NM | NM | 2.9 | 61 |

NM - value not measured; blank - compound not made

The diacid compounds of this invention are all very potent inhibitors of GST P1-1 ($IC_{50}$<20 nM, with several having $IC_{50}$<10 nM), and are also selective for GST P1-1 over GST A1-1 and GST M1-1, the two other human GST isoenzymes. The diethyl esters all show good cytotoxicity in HL-60 cells, and many show significant inhibition of GSTπ as measured in the immunoprecipitation assay.

Some of the diethyl ester compounds of this invention were also tested for their ability to enhance the differentiation of HL-60 cells. This illustrates the beneficial effect of the compounds of this invention in stimulating differentiation of the HL-60 human leukemia cell line in vitro. These results are considered predictive of efficacy in human myelostimulation, because TLK199, which enhances differentiation in this assay, has shown myelostimulant activity in humans. Log-phase cells ($1\times10^5$ cells/mL) were incubated at 37° C. under air/5% $CO_2$ for 24 hours in 2 mL of the supplemented RPMI 1640 medium used in In vitro Example 2 and the test compounds dissolved in DMSO, with a final DMSO concentration of 0.1%. The cells were harvested by centrifugation (1250 rpm for 5 min at 20° C.) and washed with 2 mL ice-cold phosphate-buffered saline (PBS) containing 2% FBS, then stained with 10 µL phycoerythrin-conjugated anti-CD11b antibody or 10 μL phycoerythrin-conjugated isotype control antibody. After standing for 30 min on ice, the cells were re-suspended in 2 mL ice-cold PBS containing 2% FBS. The cells were harvested by centrifugation (1250 rpm for 5 min at 20° C.) and resuspended in 0.4 mL PBS containing 2% FBS. The specific cell surface expression of CD11b, a marker for granulocytes and monocytes, was detected by flow cytometry using a FACSCalibur analyzer (BD Biosciences). All assays were conducted in triplicate, with DMSO control. The extent of differentiation was expressed as a multiple of the signal from the DMSO control. Several of the tested compounds enhanced the differentiation of HL-60 cells.

From these results and the structural similarity of these compounds to TLK199, the compounds, especially as the diesters, are expected to act therapeutically to: potentiate the cytotoxic effects of chemotherapeutic agents in tumor cells, selectively exert cytotoxicity in tumor cells, elevate the production of GM progenitors in bone marrow, stimulate the differentiation of bone marrow, mitigate the myelosuppressive effects of chemotherapeutic agents, and modulate hematopoiesis in bone marrow.

Formulation Example. This example illustrates suitable formulations for the compounds of this invention, especially the diesters.

A solid formulation for oral administration is prepared by combining the following:

| | |
|---|---|
| Compound | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 250 mg of the compound. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

A formulation for IV administration is prepared by dissolving the compound, for example as a pharmaceutically acceptable salt, to a concentration of 1% w/v in phosphate-buffered saline; and the solution is sterilized, for example by sterile filtration, and sealed in sterile containers containing, for example, 250 mg of a compound of this invention.

Alternatively, a lyophilized formulation is prepared by dissolving the compound, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized formulation is reconstituted by the addition of sterile water, and the reconstituted solution may be further diluted for administration with a solution such as 0.9% sodium chloride intravenous infusion or 5% dextrose intravenous infusion.

Alternatively, a liposomal formulation is prepared by the method of U.S. Published Application No. 2003/0100511 (e.g. Examples 4 and 5) using a compound of this invention in place of compound 9 of that publication, and may be lyophilized as described in that publication.

Therapeutic Example. This example illustrates a suitable therapeutic method for the compounds of this invention.

A compound of this invention, in an intravenous formulation as described in the Formulation Example above, is administered intravenously over 30 minutes to a patient suffering from myelodysplastic syndrome at an initial dose of 50 mg/m$^2$; and this dose is increased to 100 mg/m$^2$, 200 mg/m$^2$, 400 mg/m$^2$, and 600 mg/m$^2$. The compound is administered once per day for five days every three weeks.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A compound of the formula

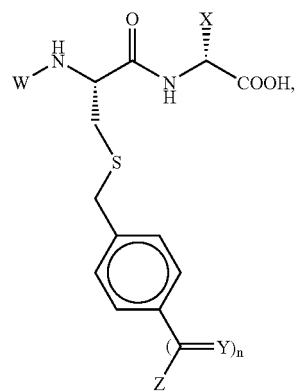

or its $C_{1-10}$ alkyl, phenyl-$C_{1-3}$ alkyl, or ($C_{5-6}$ heteroaryl)-$C_{1-3}$ alkyl mono- or di-ester, or a salt of the compound or its mono- or di-ester where:

n is 0 or 1;

W is L-γ-glutamyl or L-γ-glutamylglycyl;

X is optionally substituted $C_{5-6}$ cycloalkyl, optionally substituted $C_{5-6}$ heterocycloalkyl, optionally substituted phenyl, or optionally substituted $C_{5-6}$ heteroaryl;

Y is =O, =N—OH, or =N—O(optionally substituted $C_{1-3}$ alkyl); and

Z is optionally substituted phenyl or optionally substituted $C_{5-6}$ heteroaryl.

2. The compound of claim 1 where n is 0.

3. The compound of claim 1 where n is 1.

4. The compound of claim 3 where Y is =O.

5. The compound of claim 1 where W is L-γ-glutamyl.

6. The compound of claim 1 where X is cyclopentyl, cyclohexyl, thienyl, furyl, pyridinyl, or optionally substituted phenyl.

7. The compound of claim 6 where X is cyclohexyl.

8. The compound of claim 6 where X is phenyl, optionally substituted with 1 or 2 fluoro, chloro, methyl, hydroxy, methoxy, or trifluoromethyl groups.

9. The compound of claim 8 where the phenyl is unsubstituted.

10. The compound of claim 8 where the phenyl is substituted and one of the substituents is in the 4-position.

11. The compound of claim 10 where there is only one substituent.

12. The compound of claim 1 where the —C(=Y)$_n$—Z substitution is on the 2- or 4-position of the phenyl group.

13. The compound of claim 12 where the —C(=Y)$_n$—Z substitution is on the 2-position of the phenyl group.

14. The compound of claim 12 where the —C(=Y)$_n$—Z substitution is on the 4-position of the phenyl group.

15. The compound of claim 14 where Z is phenyl, optionally substituted with fluoro, chloro, cyano, methyl, hydroxy, methoxy, or trifluoromethyl.

16. The compound of claim 1 that is a diacid, or a salt thereof.

17. The compound of claim 1 that is a diester, or a salt thereof.

18. The compound of claim 17 that is a $C_{1-6}$ alkyl or benzyl diester, or a salt thereof.

19. The compound of claim 18 that is a $C_{1-3}$ alkyl diester, or a salt thereof.

20. The compound of claim 19 that is a diethyl ester, or a salt thereof.

21. The compound of claim 1 that is selected from:
L-γ-glutamyl-S-[(4-biphenylyl)methyl]-L-cysteinyl-D-phenylglycine,
L-γ-glutamyl-S-[(2-biphenylyl)methyl]-L-cysteinyl-D-phenylglycine,
L-γ-glutamyl-S-[(2'-cyano-4-biphenylyl)methyl]-L-cysteinyl-D-phenylglycine,
L-γ-glutamyl-S-[(2'-methoxy-4-biphenylyl)methyl]-L-cysteinyl-D-phenylglycine,
L-γ-glutamyl-S-[(3'-(trifluoromethyl)-4-biphenylyl)methyl]-L-cysteinyl-D-phenylglycine,
L-γ-glutamyl-S-[(4'-carboxy-4-biphenylyl)methyl]-L-Cysteinyl-D-phenylglycine,
L-γ-glutamyl-S-[(4'-cyano-4-biphenylyl)methyl]-L-Cysteinyl-D-phenylglycine,
L-γ-glutamyl-S-{[4-(2-pyridyl)phenyl]methyl}-L-cysteinyl-D-phenylglycine,
L-γ-glutamyl-S-[(4-benzoylphenyl)methyl]-L-cysteinyl-D-phenylglycine,
L-γ-glutamyl-S-({4-[(2-aminoethoxyimino)(phenyl)methyl]phenyl}methyl)-L-cysteinyl-D-phenylglycine,
L-γ-glutamyl-S-[(4-biphenylyl)methyl]-L-Cysteinyl-D-(4-chlorophenyl)glycine, and
L-γ-glutamyl-S-[(4-biphenylyl)methyl]-L-cysteinyl-D-cyclohexylglycine,
and their diethyl esters,
and the salts of the compounds and their diethyl esters.

22. A pharmaceutical composition comprising a compound of claim 1 and an excipient.

23. A method of potentiating the cytotoxic effects of chemotherapeutic agents in tumor cells, elevating the production of GM progenitors in bone marrow, stimulating the differentiation of bone marrow, mitigating the myelosuppressive effects of chemotherapeutic agents, or modulating hematopoiesis in bone marrow, comprising administering a compound of claim 1.

24. A compound of the formula

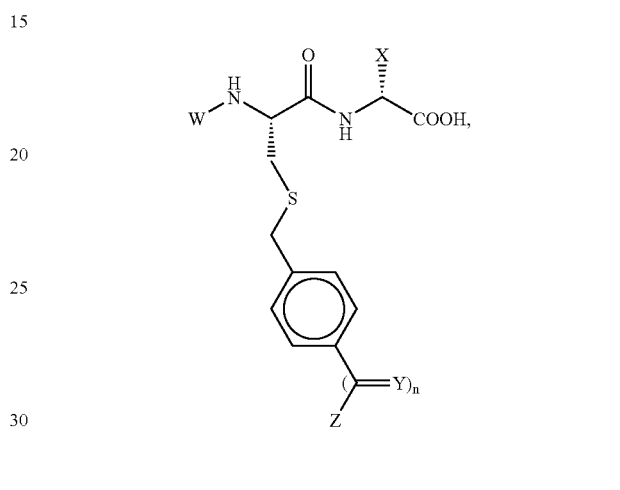

or its $C_{1-10}$ alkyl, phenyl-$C_{1-3}$ alkyl, or ($C_{5-6}$ heteroaryl)-$C_{1-3}$ alkyl mono- or di-ester, or a salt of the compound or its mono- or di-ester where:
W is N-α-$R^1$-L-γ-glutamyl or N-α-$R^1$-L-γ-glutamylglycyl, where $R^1$ is an amine-protecting group; and
n, X, Y and Z are as defined in claim 1.

* * * * *

UNITED STATES PATENT AND TRADEMARK OFFICE
CERTIFICATE OF CORRECTION

PATENT NO. : 7,129,215 B2 Page 1 of 1
APPLICATION NO. : 11/325846
DATED : October 31, 2006
INVENTOR(S) : Aurrecoechea et al.

It is certified that error appears in the above-identified patent and that said Letters Patent is hereby corrected as shown below:

Column 7,
Line 30, "Z–C(=Y)$_n$–" should read -- Z–(C=Y)$_n$– --;

Column 26,
Line 66, "–C(=Y)$_n$–Z" should read -- –(C=Y)$_n$–Z --;

Column 27,
Line 1, "–C(=Y)$_n$–Z" should read -- –(C=Y)$_n$–Z --;

Line 3, "–C(=Y)$_n$–Z" should read -- –(C=Y)$_n$–Z--.

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,129,215 B2  
APPLICATION NO. : 11/325846  
DATED : October 31, 2006  
INVENTOR(S) : Natalia Aurrecoechea et al.

Page 1 of 4

It is certified that error appears in the above-identified patent and that said Letters Patent is hereby corrected as shown below:

IN THE SPECIFICATION

Column 4, lines 5-23,

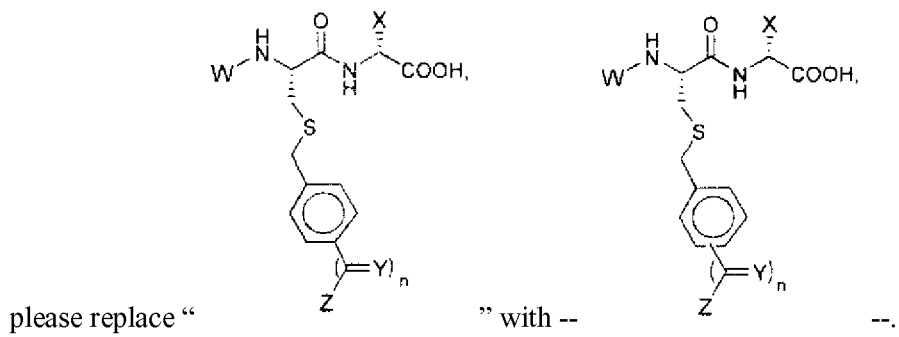

please replace " " with -- --.

Column 5, lines 3-18,

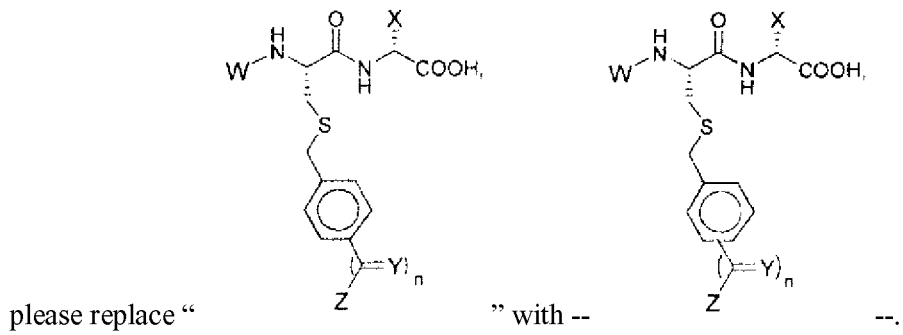

please replace " " with -- --.

Signed and Sealed this
Fourteenth Day of August, 2012

David J. Kappos
*Director of the United States Patent and Trademark Office*

CERTIFICATE OF CORRECTION (continued)
U.S. Pat. No. 7,129,215 B2

Column 6, lines 46-63, please replace " 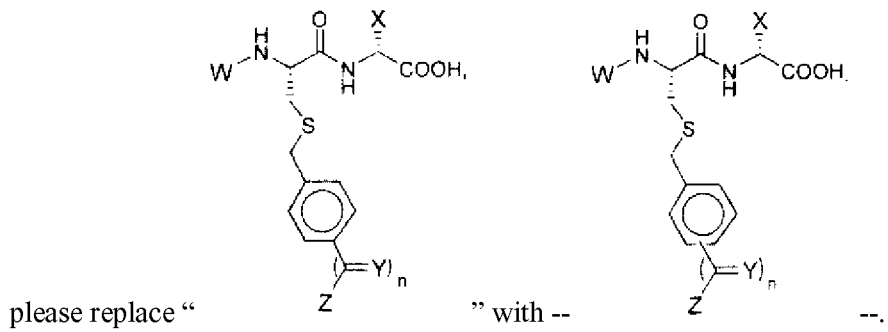 " with -- --.

Column 8, lines 18-29, please replace " 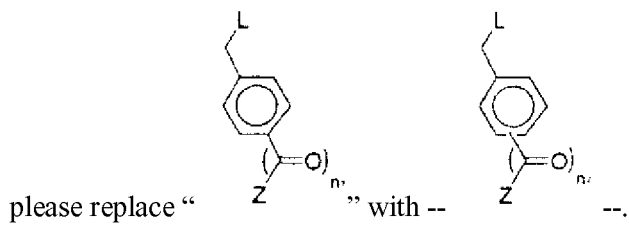 " with -- --.

Column 8, lines 39-53, please replace " 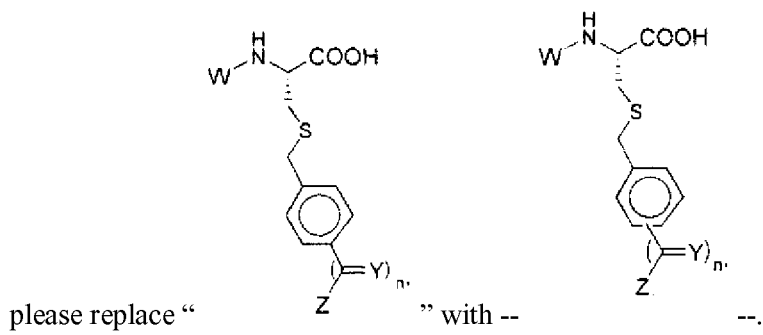 " with -- --.

Column 9, lines 3-21, please replace " 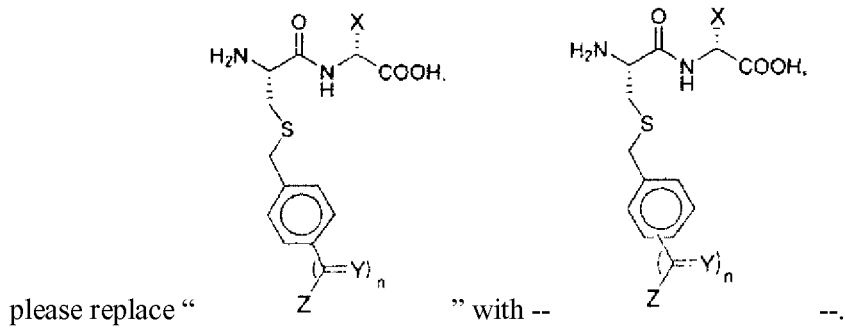 " with -- --.

CERTIFICATE OF CORRECTION (continued)
U.S. Pat. No. 7,129,215 B2

Column 9, lines 48-63, please replace " 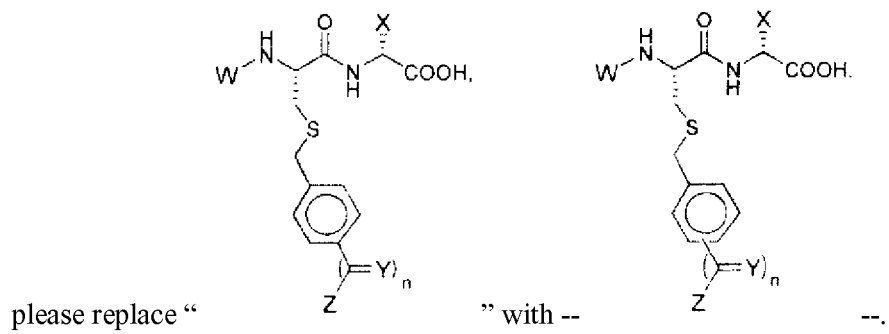 " with -- --.

Column 11, lines 44-55, please replace " 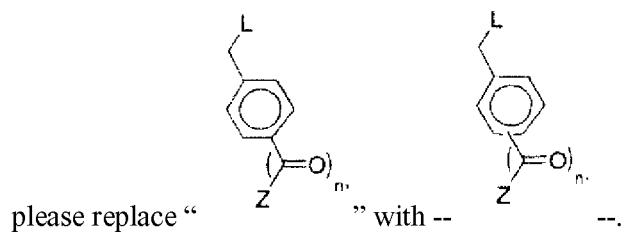 " with -- --.

Column 12, lines 25-37, please replace " 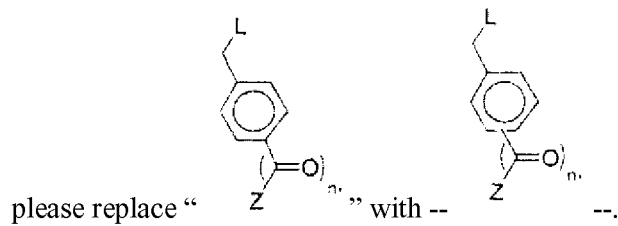 " with -- --.

IN THE CLAIMS

In Claim 1, column 26, lines 17-33, please replace " 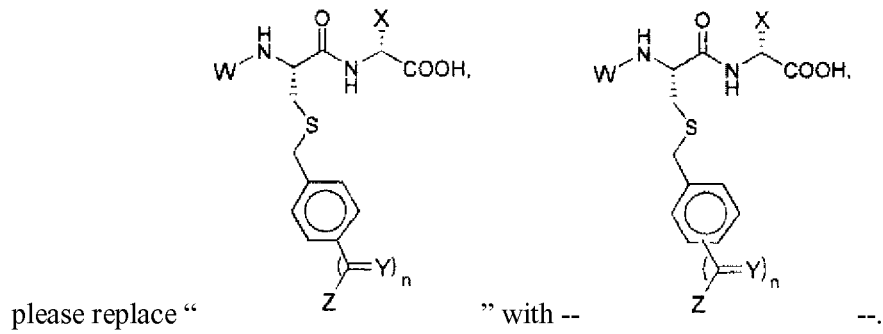 " with -- --.

CERTIFICATE OF CORRECTION (continued)
U.S. Pat. No. 7,129,215 B2

In Claim 24, lines 15-31,

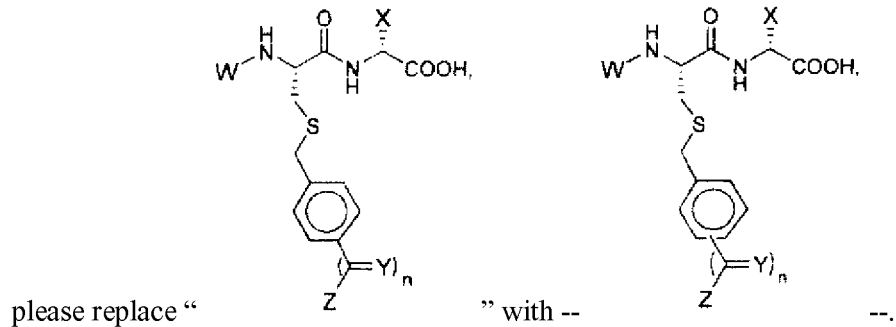

please replace " [structure] " with -- [structure] --.